United States Patent [19]
Hirano et al.

[11] Patent Number: 5,652,395
[45] Date of Patent: Jul. 29, 1997

[54] BENDING SENSOR

[75] Inventors: Teruaki Hirano; Nozomu Kikuchi, both of Tokyo; Kazumasa Saito, Saitama, all of Japan

[73] Assignee: Hirano Electronics Co. Ltd., Tokyo, Japan

[21] Appl. No.: 654,908

[22] Filed: May 29, 1996

[30] Foreign Application Priority Data

Jun. 19, 1995 [JP] Japan ................. 7-151967

[51] Int. Cl.⁶ ............................................ G01N 3/20
[52] U.S. Cl. ............................ 73/849; 73/762; 73/775
[58] Field of Search ........................ 73/762, 775, 776, 73/777, 849, 851

[56] References Cited

U.S. PATENT DOCUMENTS

| | | | |
|---|---|---|---|
| 3,738,162 | 6/1973 | Dally et al. | 73/775 |
| 3,803,485 | 4/1974 | Crites et al. | 73/762 X |
| 4,002,060 | 1/1977 | Ogata et al. | 73/762 |
| 4,047,144 | 9/1977 | Wong | 73/777 X |
| 4,085,949 | 4/1978 | Asao et al. | 73/762 X |
| 4,715,235 | 12/1987 | Fukui et al. | 73/775 X |
| 5,086,652 | 2/1992 | Kropp | 73/767 |
| 5,192,938 | 3/1993 | Ort | 73/778 X |
| 5,325,721 | 7/1994 | Pendergrass, Jr. | 73/762 |
| 5,533,391 | 7/1996 | Brade et al. | 73/170.19 |

FOREIGN PATENT DOCUMENTS 4-233442  8/1992  Japan .
939282  10/1963  United Kingdom .

*Primary Examiner*—Elizabeth L. Dougherty
*Attorney, Agent, or Firm*—Kanesaka & Takeuchi

[57] ABSTRACT

A bending sensor of the invention is formed of a flexible segment, a pressure-sensitive electrically-conductive resin film formed on the flexible segment, and a pair of electrodes to be attached to the resin film. The resin film is made of pressure-sensitive electroconductive ink and coated on the segment. The resin film has a characteristic such that an electric resistance value is reduced as a pressure on the resin film increases. When the segment is bend-formed at an inflection point by receiving an outer force, the segment provides a pressure to the resin film at the inflection point to produce an inner stress in the resin film. When the segment is bent-deformed, the electrodes output a resistance change of the resin film to thereby detect bending of the flexible segment.

5 Claims, 4 Drawing Sheets

BENDING SENSOR

BACKGROUND OF THE INVENTION

1. Field of the Invention

The present invention relates to a bend-detecting sensor (hereinafter referred to as "bending sensor") which is used for detecting bent or deformed portions of machines and tools and bending-angles of human bodies' joints.

2. Description of Prior Art

It has been conventionally known an electric-resistance strain gauge as means to measure a degree and distribution of stress and load formed at a part of a machine or a structure, and deformed state of mechanical components and the like. There have been known various kinds of methods and machines used for the measurement of strain. Among them, it has been said that measuring means using a strain gauge is most accurate means.

In the strain gauge, a metal-resistance body which is photo-optically etched is bonded on a film-shaped resin and a leading wire is drawn out of the metal-resistance body. Strain which occurs in a substance to be measured is converted into change in resistance to be outputted. In other words, strains ocurring in the substance to be measured are transferred to the metal-resistance body via the film-shaped resin which is a base, and the metal-resistance body is deformed in response to the degree of strain, causing change in resistance, which is taken out as an output. The output of the strain gauge is detected by, for example, Wheatstone bridge circuit and "strain amount" caused in a substance to be measured is calculated by the output voltage of the Wheatstone bridge circuit. The strain gauge is used for industrially testing the strength of a material and for analysis in structure-mechanism of civil engineering and construction, and used as elements of various kinds of transducers and as sensors of control machines or tools in an automobile.

The principle of the strain sensor is utilized for detecting movement of a human body or a movement of a finger. For example, Japanese Patent Application Laid-open No. Hei 4-233442 (JP-A-4-233442) discloses a bending sensor which comprises an elastic body and has a construction such that a resistance-body is provided inside the elastic body and a neutral face at bending of the resistance-body and a neutral face at bending of the elastic body are placed in the vicinity where the both neutral faces do not coincide.

The resistance-body used in the invention of the Japanese Patent Application Laid-open No. Hei 4-233442 is identical with the metal-resistance body of the aforesaid strain sensor. The bending sensor is set on a necessary part of a body of a player who plays a piano, a guitar, etc. When the player' body is bent, the bending sensor detects the bending-degree and generates detecting signals. The detecting signals are outputted to the outside. As one of an application of the bending sensor, for example, there is a wearing tool in a form of a glove in which each bending sensor is fitted to the backface of each finger of the glove. When a player wearing the fitting tool performs a music in a musical instrument, a detected output as to how fingers are moved at the musical performance can be obtained.

However, the above-described bending-sensor has such problems that the metal-resistance body which is used for detecting the bending of a substance to be measured is not necessarily great in regard to an amount of change in resistance by strain and that when bending-deformation is repeated to the metal-resistance body, the life of the resistance-change is lowered by metal fatigue due to the fact that the metal-resistance body is made of a metal. Japanese Patent Application Laid-open No. Hei 4-233442 intends to reduce the metal fatigue of its sensor by relatively largely setting the shift of positions of the neutral face at bending of the resistance body and the neutral face at bending of the elastic body so as to reduce the strain amount. However, even though the metal fatigue is reduced, it is only a degree of reduction.

The problem of metal fatigue has not be solved fundamentally. As contrast from Japanese Patent Application Laid-open No. Hei 4-233442 in which the metal resistance body is adhered to the base member by an adhesive, the metal resistance body can be formed on the base member by using sputtering method.

However, the sputtering method requires high technology and in any way, as long as the sensor uses a metal-resistance body, metal fatigue is generated; and unless this problem is not solved, the sensor made of a metal material is not necessarily effective for detecting a large bending.

SUMMARY OF THE INVENTION

The object of the present invention is to provide a bending sensor which is effective for measuring bending-deformation in which bending ratio is great.

In order to achieve the above-mentioned object, in a bending-sensor of the present invention, a pressure-sensitive electrically-conductive resin film is provided on a segment so that change in resistance produced at the pressure-sensitive electrically-conductive resin film is detected via an electrode.

The pressure-sensitive electrically-conductive resin film is formed by coating a pressure-sensitive electroconductive ink. The film has a characteristic such that the resistance-change is reduced in accordance with the pressurization on the input face.

The segment has flexibility and is bent and deformed by receiving an outer force. The segment provides pressure to the pressure-sensitive electrically-resin film at the point of inflection produced by the bending-deformation to produce an inner stress.

The electrode is constituted by a pair of electrodes and the electrodes output the resistance-change of the pressure-sensitive electrically-conductive resin film at the bending-deformation of the segment to the outside.

Moreover, in the bending-sensor of the present invention, the segment has an oblong shape and is arranged to be inflectively deformed in a transverse direction at right angle or at an angle with respect to the longitudinal direction of the segment. The pressure-sensitive electrically-conductive resin film is provided on the segment with the same width along the almost whole length of the segment and with a constant width.

The electrodes are provided on the base plate. The base plate is flexible and is an oblong shape. The base plate is piled on the segment and is bend-deformed together with the segment. The pressure-sensitive electrically-conductive resin film on the segment and the electrodes on the base plate are opposed to each other at a predetermined distance. The pair of electrodes contact the pressure-sensitive electrically-conductive resin film to output resistance-change at the time of bending-deformation to the outside.

Each electrode has comb-blade shaped portions which are diverged and extend in the longitudinal direction of the base plate. The comb-blade shaped portions of the electrodes are alternately arranged to each other.

The segment and the base plate are integrally piled via a layer of an adhesive which is mounted on the periphery of the pressure-sensitive electrically-conductive resin film and electrode-forming region, or a double-sided adhesive tape.

DETAILED DESCRIPTION OF PREFERRED EMBODIMENT

A sensor which detects the action of a body or fingers is a sensor which detects strain partially generated by bending-deformation and is theoretically the same with a strain-gauge used to measure stress of constructions and machines, degree of load and deformed state of members.

In the present invention, a pressure-sensitive electroconductive ink is used as a resistance body of the bending-sensor. The pressure-sensitive electroconductive ink is prepared by compounding electroconductive grains in a polymer such as silicone polymer. The pressure-sensitive electroconductive ink is printed on a plastic film by a screen printing, which is known as a new type of a pressure-sensitive resistance element. For example, the pressure-sensitive resistance element is sold in the name of "Siltouch 100", "Siltouch 200" and "Silktouch 300" by Toshiba Silicone Kabushiki Kaisha ( "Siltouch": product name).

Figure 1:
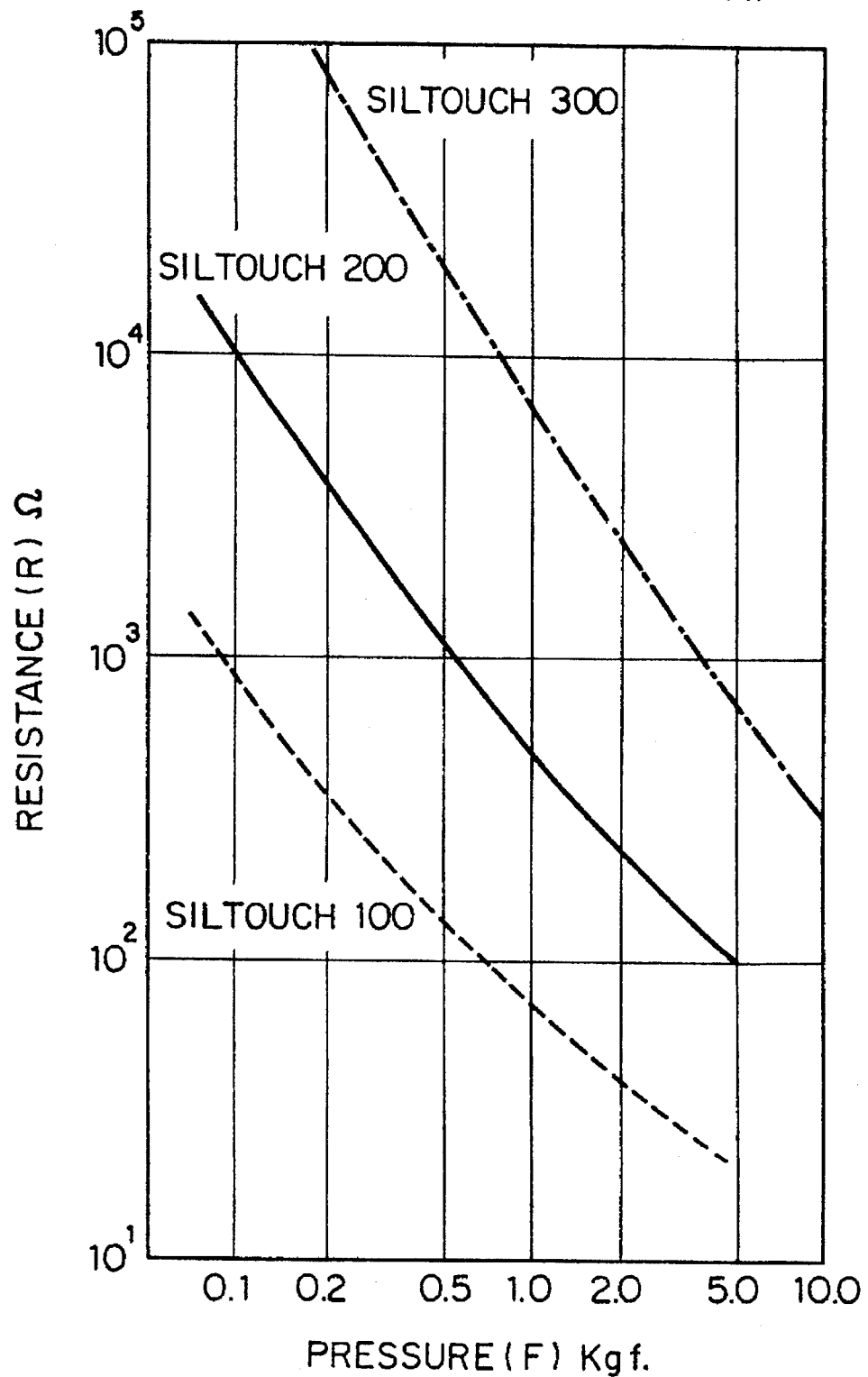
FIG. 1 is a graph showing pressure-resistance property of Siltouch (100, 200, 300).

This pressure-sensitive resistance element is expected to be applied in a field of a tablet, a sensor of striking keys, connectors as a pressure-sensor. The pressure-sensitive resistance element has its characteristic that a resistance value is reduced as the input face is given pressure. The relative relationship of pressure-resistance property (F-R property) has been said to be almost "F∝R$^{-1}$". FIG. 1 shows the representative pressure-resistance property of "Siltouch 100", "Siltouch 200" and "Siltouch 300" of Toshiba Silicone Kabushiki Kaisha. (catalogue of Toshiba Silicone Kabushiki Kaisha "Siltouch" which is new sensitive pressure-resistance element prepared by applying a pressure-sensitive electroconductive ink and a screening printing technology).

FIG. 1 illustrates a relationship between resistance-change and pressure in a case that pressure is given to the sensitive pressure-resistance element in a state that a measuring current is constantly given at 0.1 mA in measuring the resistance-change.

In the above-mentioned pressure-sensitive resistance element, the resistance value of the printing film changes as the input face receives pressure. The present invention utilizes this pressure-resistance property in measuring the bending-deformation of a member. When the segment provided with the pressure-sensitive electrically-conductive resin film prepared by the pressure-sensitive electroconductive ink is deformed concavedly or convexedly against the elasticity of the segment, internal stress is produced in the pressure-sensitive electrically-conductive resin film of the inflective-deformed portion. This internal stress is substantially the same as the internal stress caused by pressurizing the input face and therefore, resistance value is changed in response to the degree of stress generated by the inflective-deformation of the pressure-sensitive electrically-conductive resin. When the segment is deformed, the base plate is inflectively deformed together with the segment, and the change of the resistance value in the pressure-sensitive electrically-conductive resin which is generated around the inflection point concavedly or convexedly inflective-deformed is taken out to the outside as signals via the electrodes.

Now, an example of the present invention is explained referring to the attached drawings.

Figure 2:
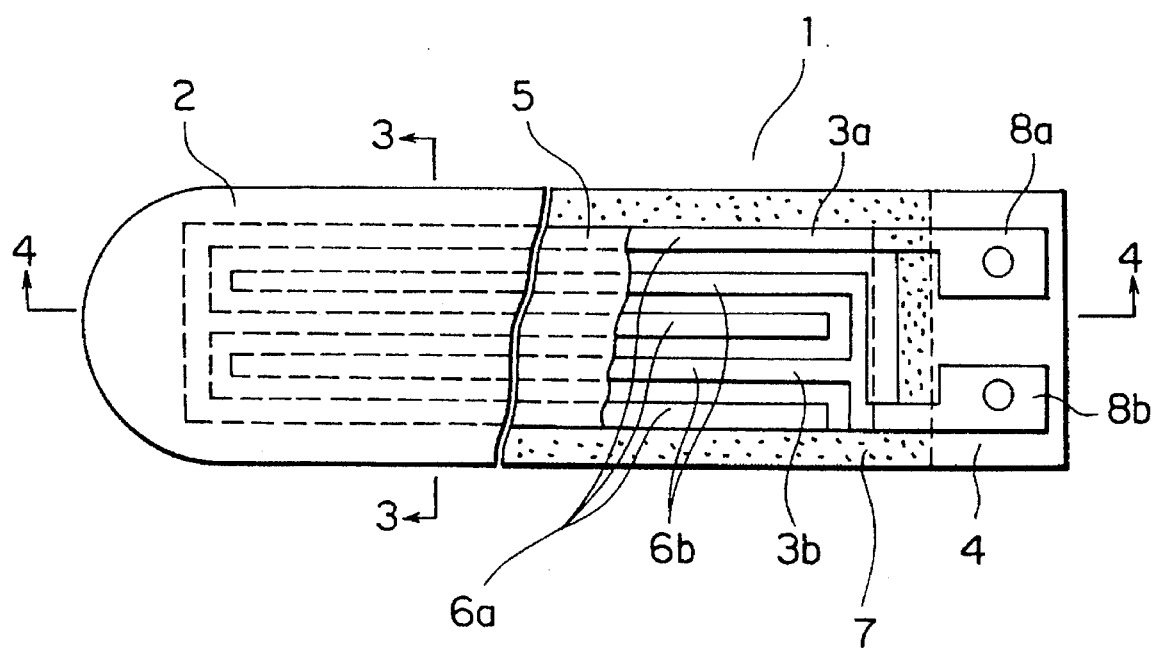
FIG. 2 is a partially cross-sectional plan view showing one example of a bending sensor according to the present invention.

In FIG. 2, a bending sensor 1 according to the present invention has a combination of a segment 2 which is provided with a pressure-sensitive electrically-conductive resin film 5 on one side and a base plate 4 which is provided with a pair of electrodes 3a and 3b on one side. The segment 2 and the base plate 4 are insurated films having flexibility and manufactured in an oblong shape. The whole length of the base plate 4, is made slightly longer than the segment 2. As the segment 2, for example, a polyester resin film is used. As the base plate for example, a polyester resin film or a polyimide resin film is used. However, as long as the film has electrical insulation, flexbilitiy and restoration to the original shape and size after being deformed, it can be used in the present invention without relating to transparency of the film.

The pressure-sensitive electrically-conductive resin film 5 is formed by coating a pressure-sensitive electroconductive ink (for example, pressure-sensitive electrically-conductive inks used in Siltouch 100, Siltouch 200 or Siltouch 300 produced by Toshiba Silicone Kabushiki Kaisha) on one side face of the segment 2. In making the coating, the pressure-sensitive electroconductive ink is coated and hardened on an oblong region of the segment 2 in the form of long strip except for a peripheral edge portion of the segment 2 which becomes a portion to be adhered.

The electrodes 3a, 3b are provided in the oblong region of the base plate 4 corresponding to the region where the pressure-sensitive electrically-conductive resin film 5 is formed. A pair of the electrodes 3a, 3b is formed by etching an electrically-conductive film laminated on the base plate 4 or by screen-printing an electroconductive ink on the base plate 4. An electrode terminal 8a of the electrode 3a and an electrode terminal 8b of the electrode 3b are provided at one end in the longitudinal direction of the base plate 4. Each of the electrodes 3a and 3b is branched into two or more. The branched portions extend in a form of comb-blade in the longitudinal direction of the base plate 4 and the comb-blade shaped portions 6a, 6b of each electrode 3a or 3b are alternately and adjacently arranged.

Figure 3:
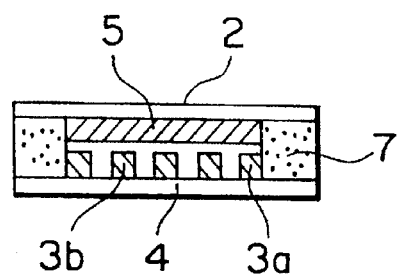
FIG. 3 is a cross-sectional view taken along a line 3—3 in FIG. 2.

An adhesive having stickiness is coated on the base plate 4 at the peripheral edge portion around the region of the electrodes 3a, 3b in a manner that the adhesive exceeds above the height of the electrodes 3a, 3b. A double-sided adhesive tape may be used instead of the adhesive. The segment 2 is put on the adhesive in such a manner that a face forming the pressure-sensitive electrically-conductive resin film 5 is faced downwardly and the segment 2 is adhered to an adhesive layer 7 by piling up the adhesive. Electrode terminals 8a, 8b are formed on an exposed portion of the laminated base. Thus, the bending sensor 1 is obtained. By this structure, the base plate 4 and the segment 2 are integrally laminated, and the electrodes 3a, 3b and the pressure-sensitive electrically-conductive resin film 5 are arranged to face each other with a gap as shown in FIG. 3.

Figure 4:
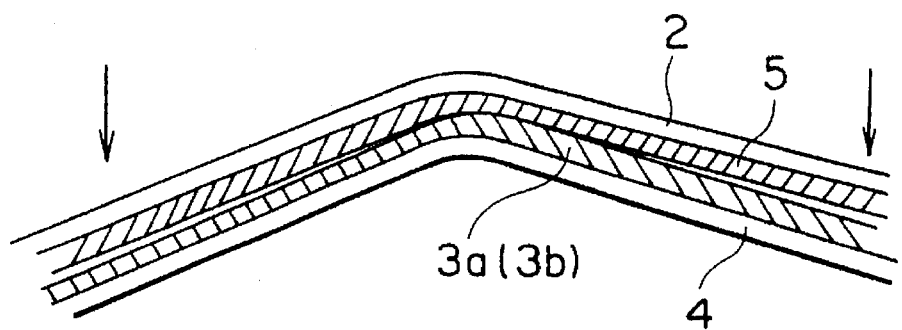
FIG. 4 is a cross-sectional view taken along a line 4—4 in FIG. 1 showing a state when the bending sensor is inflective-deformed.
Figure 5:
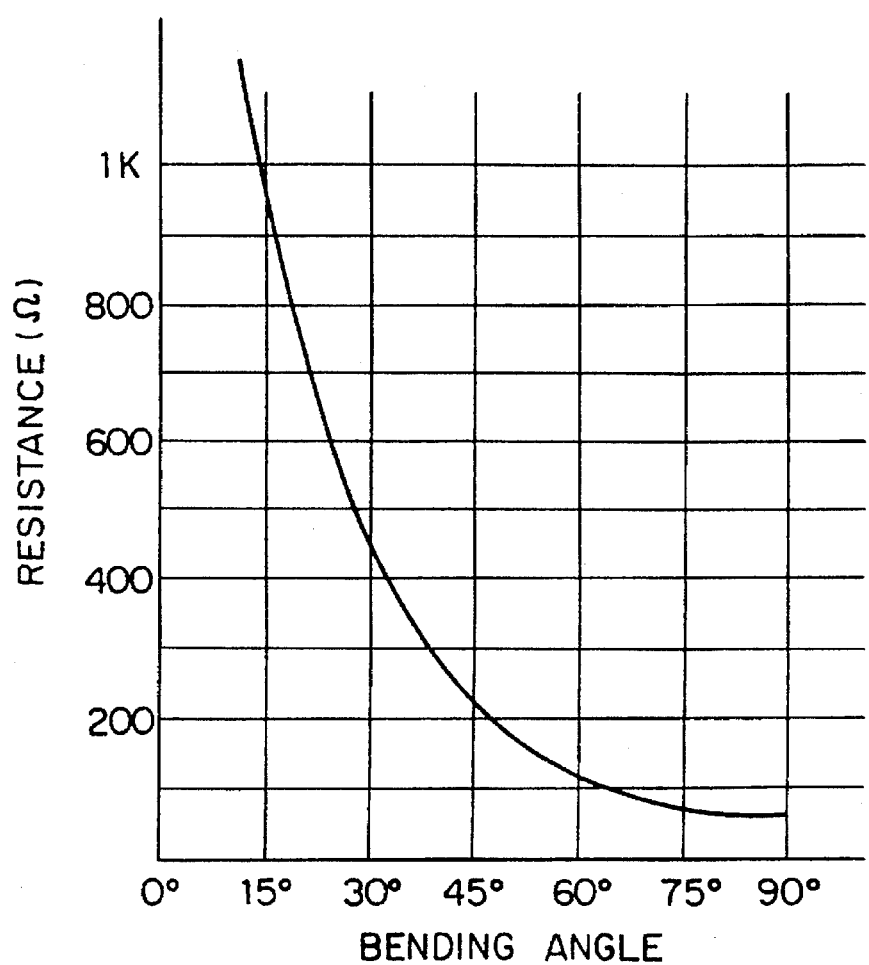
FIG. 5 is a view showing one example of resistance-change property with respect to a bending angle by the bending sensor of the present invention.

In the example, when the bending sensor 1 of the present invention is inflectively deformed at a right angle or at an angle in a longitudinal direction thereof as shown in FIG. 4, a bent-convex portion or bent-concave portion at an inflection point which is formed by the bending is pressed, and inner stress is loaded on the bending sensor, whereby the bending sensor's resistance changes. At the same time, a parts of the electrodes 3a, 3b are pressed against a part of the pressure-sensitive electrically-conductive resin film 5 and the resistance change is taken out to the outside through the electrode terminals 8a, 8b. The pressure-sensitive electrically-conductive resin film 5 is reduced in its resistance value in proportion to its bending angle. FIG. 5 shows one example of resistance-change property with respect to bending angle of the pressure-sensitive electrically-conductive resin film 5. This is an example of a bending sensor in which a pressure-sensitive electrically-conductive resin film (30 mm in length, 4.5 mm in width and 20/μm in thickness) is formed on a polyester film.

Figure 6:
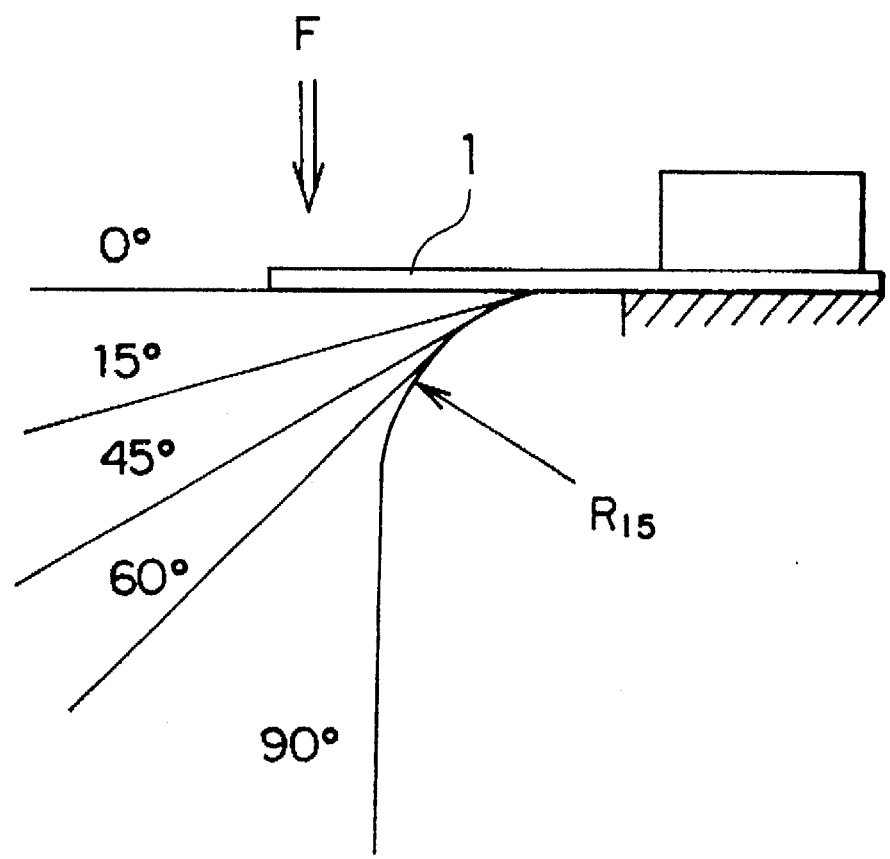
FIG. 6 is a view showing a measuring method of resistance value caused by bending deformation by the bending sensor.

The measurement was conducted by the following way. Namely, in FIG. 6, one side end of the bending sensor 1 is fixed and supported horizontally, and force F is given to the free end of the bending sensor 1, whereby the change of the resistance value which corresponds to inflective angle of 0° to 90° is measured. In this connection, the curvature of the inflective-deformation is 15 mm (R). In this example, the measurement was conducted by constantly setting the measuring current at 0.1 mA, and the resistance value was greatly changed from several KΩ to several ten Ω within the range of 15° to 90° and the bending angle within this range could be precisely measured, whereby it can be understood that the present invention is effective especially against great change of the curvature.

The example shows that in the bending sensor, the pressure-sensitive electrically-conductive resin film and the electrodes face each other with a gap and that when the bending sensor is inflectively deformed, the electrodes contact the pressure-sensitive electrically-conductive resin to change output signals in the resistance value. However, the pressure-sensitive electrically-conductive resin film and the electrodes are not necessarily separated at a time when a deformation of the bending sensor is not conducted. When the pressure-sensitive resin film and the electrodes are previously contacted, an output at a time when the bending sensor is not deformed is obtained between the electrodes, and at the bending-deforming time, an output at the deforming time can be obtained between the electrodes. When two or more inflection points are formed, the bending deformation may be, for example, deformation in which bent-convexed portion and bent-concaved portion are repeatedly formed along the direction of the bending sensor. Furthermore, if the pressure-sensitive electrically-conductive resin is formed with the same width along the whole length of the bending sensor, an output value by the bending deformation is the same at an arbitrary cross-sectional point. However, according to the object of using the bending sensor, the width can be changed along the longitudinal direction or bending strength can be partially changed.

As mentioned above, according to the present invention, a segment having flexibility is provided with a pressure-sensitive electrically-conductive resin film. Change of resistance value generated when the segment is inflective-deformed in a direction crossing at a right angle or at an angle relative to the longitudinal direction of the segment can be taken out to the outside through the electrodes of the base plate. The pressure-sensitive electrically-conductive resin in which a pressure-sensitive electroconductive ink is used is excellent in reproductivity of the pressure-resistance change property; it does not almost have hysteresis; it has excellent responsiveness; and it has a property that a resistance-value is reduced as the pressure is given to the input face. According to this structure, high precise measurement is possible at a region with a great curverture or large bending angle. Thus, for example, the present invention is especially applicable in the following uses.

1. Detection of a bending angle at joint portions such as fingers, elbows, knees of a human body.
2. Detection of a bending change in a substance, such as tire which is greatly curved by receiving loads.
3. Detection of a bending change in a substance, such as a fishing rod which is curved even by weak force.
4. Measurement of a curverture on the surface of a substance, such as a human body, a work of art, bone, etc. to which strong force can not be added.

According to the present invention, when the bending sensor is inflected, the comb-blade shaped portions of the both electrodes are short-circuited within the range of the effective length of the laminated layer prepared by laminating the segment in a form of the long strip and the base plate, and a resistance value at inflective place can be artbitrarily taken out.

Moreover, by adhering the base plate and the segment by a viscous adhesive or double-sided adhesive tape, it can absorb a relative change generated between the segment and the base plate at the bending deformation without difficulty.

What is claimed is:

1. A bending sensor comprising:

a flexible segment, a pressure-sensitive electrically-conductive resin film formed on the flexible segment, said resin film being made of pressure-sensitive electroconductive ink and coated on the segment, said resin film having a characteristic such that an electric resistance value is reduced as a pressure on the resin film increases and when the segment is bend-deformed at an inflection point by receiving an outer force, the segment provides a pressure to the resin film at the inflection point to produce an inner stress in the resin film, a pair of electrodes to be attached to the resin film, said electrodes outputting a resistance change of the resin film when the segment is bend-deformed to thereby detect bending of the flexible segment, and a flexible base portion having said electrodes thereon, said base plate having an elongated shape to be bent together with the flexible segment and being disposed such that the resin film and the electrodes are sandwiched between the segment and the base plate.

2. A bending sensor as claimed in claim 1, wherein said flexible segment has an elongated shape and is bend-formed in a direction crossing at least at an angle relative to a longitudinal direction of the flexible segment, said resin film being formed on the segment with a constant width along nearly an entire length thereof.

3. A bending sensor as claimed in claim 1, wherein each of the electrodes includes a plurality of elongated contact portions, said contact portions of the electrodes being arranged alternately along a longitudinal direction of the segment.

4. A bending sensor as claimed in claim 3, wherein said segment and the base plate are joined together at peripheries by an adhesive material so that a relative change in location between the segment and the base plate when the sensor is bent is absorbed.

5. A bending sensor as claimed in claim 3, wherein a space is formed between the electrodes and the resin film.

\* \* \* \* \*